US009717101B1

(12) United States Patent
Burnham

(10) Patent No.: US 9,717,101 B1
(45) Date of Patent: Jul. 25, 2017

(54) EMERGENCY RESPONSE SYSTEM AND METHOD FOR ELDERLY INDIVIDUALS USING MOBILE DEVICE

(71) Applicant: Andrew D. Burnham, Ballwin, MO (US)

(72) Inventor: Andrew D. Burnham, Ballwin, MO (US)

( * ) Notice: Subject to any disclaimer, the term of this patent is extended or adjusted under 35 U.S.C. 154(b) by 0 days.

(21) Appl. No.: 15/004,226

(22) Filed: Jan. 22, 2016

(51) Int. Cl.
| | | |
|---|---|---|
| H04M 11/04 | (2006.01) | |
| H04W 76/00 | (2009.01) | |
| H04W 4/22 | (2009.01) | |
| H04W 4/02 | (2009.01) | |
| H04W 4/14 | (2009.01) | |
| G06F 19/00 | (2011.01) | |

(52) U.S. Cl.
CPC ........ *H04W 76/007* (2013.01); *G06F 19/322* (2013.01); *G06F 19/3418* (2013.01); *H04W 4/021* (2013.01); *H04W 4/14* (2013.01); *H04W 4/22* (2013.01)

(58) Field of Classification Search
CPC ....... H04W 76/007; H04W 4/22; H04W 4/14; H04W 4/021; G06F 19/3418; G06F 19/322

USPC .................................. 455/404.2; 370/338
See application file for complete search history.

(56) References Cited

U.S. PATENT DOCUMENTS

| | | | | |
|---|---|---|---|---|
| 2009/0047924 | A1* | 2/2009 | Ray ................. | H04M 3/5116 455/404.2 |
| 2010/0297981 | A1* | 11/2010 | Ballantyne ........ | H04M 1/72536 455/404.2 |
| 2012/0092156 | A1* | 4/2012 | Tran .................. | G06F 19/3418 340/539.12 |
| 2015/0137972 | A1* | 5/2015 | Nepo ................ | G08B 25/016 340/539.13 |
| 2016/0019360 | A1* | 1/2016 | Pahwa .............. | G06F 19/3418 705/3 |

* cited by examiner

*Primary Examiner* — Marcos Batista

(57) ABSTRACT

The present invention is method and system that uses a mobile phone and has the ability to call and/or text one or more pre-programmed numbers once an emergency application on the mobile device is actuated without requiring any additional steps on the part of the user. In order to make this communication, the user preferably only needs to touch a simple and enlarged emergency button. The invention is catered to elderly individuals who can be prone to struggle with the functions on common mobile devices. If the user triggers the emergency call function, the mobile device will automatically call and/or text certain designated contacts of the user.

18 Claims, 8 Drawing Sheets

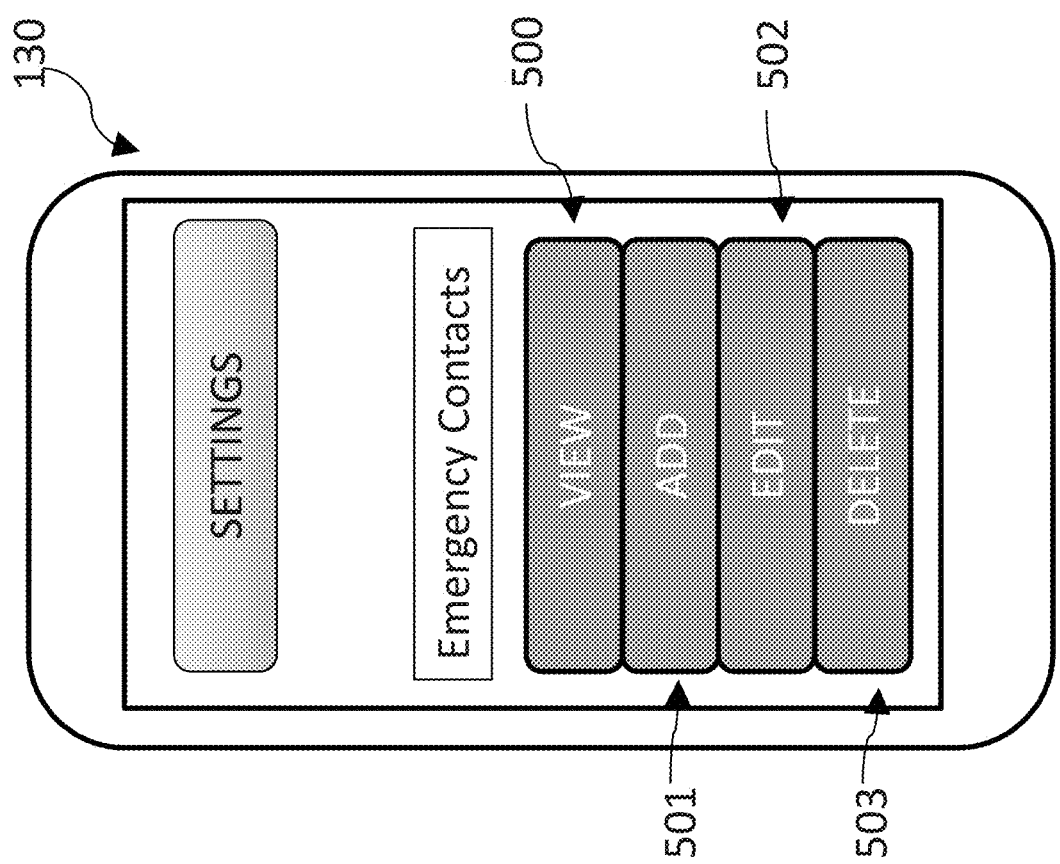

EMERGENCY RESPONSE SYSTEM AND METHOD FOR ELDERLY INDIVIDUALS USING MOBILE DEVICE

TECHNICAL FIELD

The present invention relates generally to a method and system for providing an urgent response to an emergency health condition via a mobile device. While particularly useful to elderly individuals, it can be used by any user of a mobile device.

BACKGROUND

With the recent advancements made on mobile technology, mobile devices have grown more complicated because the devices are capable of performing a large variety of tasks. However, as mobile electronic devices have increased their capabilities, their complexity has also risen dramatically. Many people are unable to perform even the simplest of tasks on mobile devices, because many of these simple actions include a series of steps requiring some familiarity with the mobile device. These complexities of modern phones can pose a serious threat in emergency situations in which an individual needs to contact someone and, in some instance, may cause lethal consequences if the person is unable to make a connection with the correct person(s) or system. Therefore, there is a need for an easily accessible emergency connection system for mobile devices.

Many elderly individuals currently use mobile devices made with the intention of having a much less complicated device. But these simpler mobile devices are not equipped with many of the most up-to-date technologies or features. Even with these simpler devices, the elderly still often struggle to operate the devices. If an emergency situation occurs, an elderly person cannot afford to struggle with establishing communications for help or assistance. When under pressure, even the simple tasks they could previously complete with ease can become much more difficult.

Furthermore, many individuals in their 60's or 70's who have grown comfortable with their current mobile devices will not be willing to trade those devices for simpler mobile devices as they age. And these more complex mobile devices, which can be currently handled by aging individuals despite of their complexities, may become more difficult to use as the person ages and loses some of their dexterity, memory, and cognitive functions.

Thus, there is a need for a system that allows user-friendly and easy wireless connectivity between an emergency-care personnel and a user's mobile device.

SUMMARY

The present invention comprises an application for a mobile phone that has the ability to call and/or text one or more pre-programmed numbers once it is opened without requiring any additional actuation on the part of the user. In order to make this communication, the user only needs to touch a simple and enlarged emergency button. The invention is catered to elderly individuals who can be prone to struggle performing functions on mobile devices. If the user triggers the emergency call function, the phone will automatically call and/or text the phone numbers of a pre-determined list of emergency contacts. The call and texts may include the user's current location, and the current vital information (heartbeat, blood pressure, etc.).

In one aspect, the present invention is a computer-implemented method for communicating an emergency condition of a user by use of a mobile device. The mobile device has network communication functionalities. The method comprises (i) by use of an emergency mobile app stored on the mobile device of the user, displaying a first on-screen button for the user to actuate in response to an emergency condition, wherein the first on-screen button is displayed on each of a plurality of pages of the mobile device; (ii) in response to actuation of the first on-screen button by the user, displaying a confirm-emergency button associated with the emergency mobile app to ensure that the user intends to send emergency communications; and (iii) in response to actuation of the confirm-emergency button by the user, automatically communicating (1) a plurality of text messages to a plurality of designated recipients indicating that the user has encountered the emergency condition, and (2) a phone call to a designated public-safety organization from which the user is requesting an emergency service.

In another aspect, the present invention is a computer-implemented method for communicating an emergency condition of a user by use of a mobile device. The mobile device has network communication functionalities. The method comprises, by use of an emergency mobile app stored on the mobile device of the user, displaying an emergency button for the user to actuate in response to an emergency condition. The emergency button is displayed on each of a plurality of display pages of the mobile device The method further includes receiving, from a monitor device, health-related data associated with the user, the monitor device including a wireless transceiver for communicating with the mobile device, and, by use of the emergency mobile app stored on the mobile device of the user, accessing the health-related data of the user. The method further includes, in response to actuation of the emergency button by the user, automatically communicating, by the mobile device, (i) a phone call to a designated public-safety organization from which the user is requesting an emergency service, and (ii) a plurality of text messages to a plurality of designated recipients indicating that the user has encountered the emergency condition, the plurality of text messages including texts that provides the current health-related data of the user.

Alternatively, the present invention is a computer-implemented method for communicating an emergency condition of a user by use of a mobile device. The method comprises (i) downloading, to the mobile device, an emergency mobile app, (ii) by use of an input device associated with the mobile device, receiving and storing user information for the emergency mobile app that can be used for emergency communications in the event of a future emergency condition, wherein the user information including contact information for contacts that are to be contacted in the event of a future emergency condition, the user information including health-related information that corresponds to the user's health condition, (iii) displaying, on the display screen of the mobile device, an emergency button associated with the emergency mobile app, the emergency button being actuatable by the user in response to an emergency condition, wherein the emergency button being displayed on each of a plurality of display pages of the mobile device, and (iv) after the emergency button has been actuated, automatically communicating, by the mobile device, (1) a plurality of text messages to at least one designated recipient indicating that the user has encountered the emergency condition, and (2) a phone call to a designated public-safety organization from which the user is requesting an emergency service, at least one of the plurality of text messages and the phone call including the health-related information that was previously entered by the user via the emergency mobile app.

The present invention is also a system for communicating an emergency condition of the user. The system includes a mobile device, a health-care monitoring device including a wireless transceiver for communicating with the mobile device, and an application stored in a storage device and downloadable via a network connection to the mobile device associated with the subject. The application when executed by the mobile device is operable to (i) permit entry of information by the user, (ii) store data related to the health-care monitoring device, (iii) display, on the display screen of the mobile device, an emergency button that is actuatable by the user in response to an emergency condition, and (iv) after the emergency button has been actuated, automatically communicate (1) a plurality of text messages to at least one designated recipient indicating that the user has encountered the emergency condition, and (2) a phone call to a designated public-safety organization from which the user is requesting an emergency service.

Further, the present invention is also a system for communicating an emergency condition of the user. The system includes a mobile device and an application downloadable via a network connection to the mobile device associated with the subject. The application when executed by the mobile device is operable to (i) permit entry of the information by the user, (ii) display, on the display screen of the mobile device, an emergency button that is actuatable by the user in response to an emergency condition, and (iii) after the emergency button has been actuated, automatically communicate (1) a plurality of text messages to at least one designated recipient indicating that the user has encountered the emergency condition, and (2) a phone call to a designated public-safety organization from which the user is requesting an emergency service.

Additionally, the automatic emergency communications can include location data of the user. The phone communication may include a prerecorded message that explains the location of the user, the user's current health condition, and/or the user's current medical condition and/or medications.

Still other aspects, features, and advantages of the present invention are readily apparent from the following detailed description, by illustrating a number of exemplary embodiments and implementations, including the best mode contemplated for carrying out the present invention. The present invention is also capable of other and different embodiments, and its several details can be modified in various respects, all without departing from the spirit and scope of the present invention. Accordingly, the drawings and descriptions are to be regarded as illustrative in nature, and not as restrictive. The invention is to cover all modifications, equivalents, and alternatives falling within the spirit and scope of the invention.

BRIEF DESCRIPTION OF THE DRAWINGS

This patent or application file contains at least one drawing executed in color. Copies of this patent or patent application publication with color drawings will be provided by the Office upon request and payment of the necessary fee.

Exemplary embodiments are illustrated in referenced figures. It is intended that the embodiments and figures disclosed herein are to be considered illustrative rather than restrictive.

FIG. 7A illustrates a first settings screen associated with the emergency application that permits the user to enter and change various pieces of information related to the designated emergency contacts.

DESCRIPTION OF ILLUSTRATED EMBODIMENTS

Figure 1:
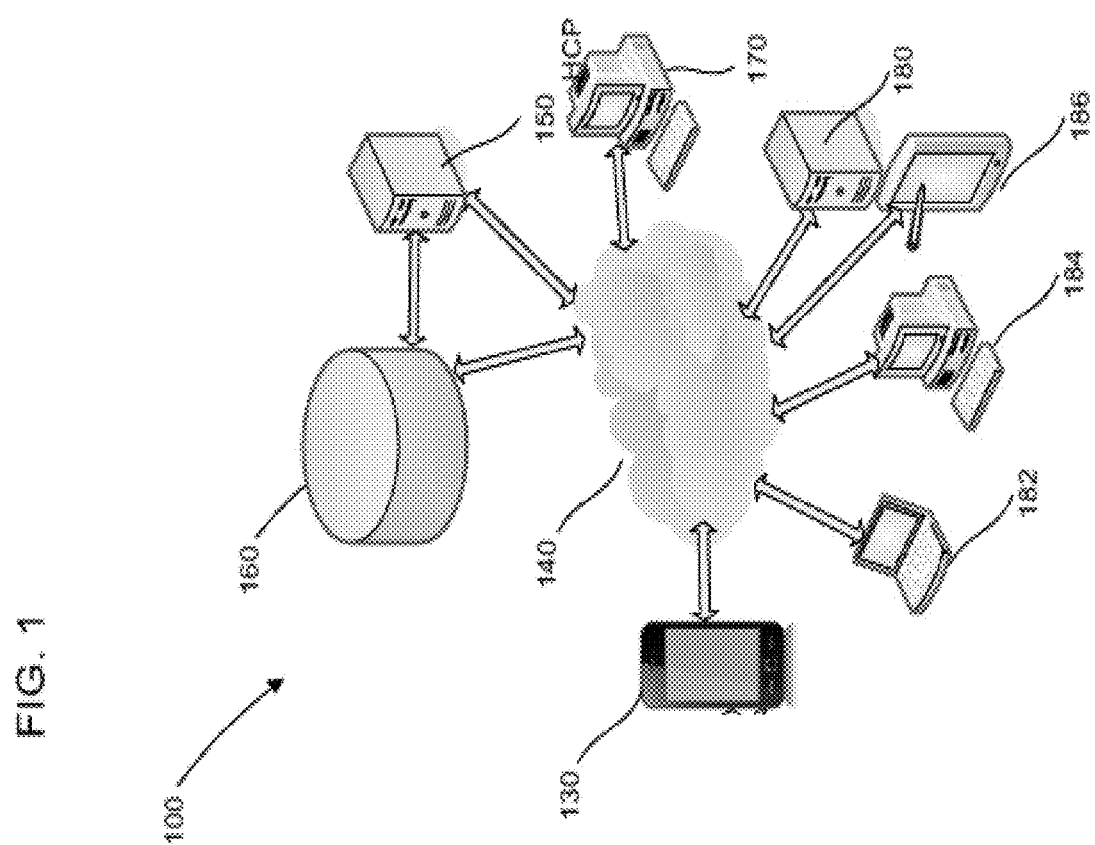
FIG. 1 illustrates a data collection system including a mobile device for use in providing an emergency alert for a use of the device.

FIG. 1 shows a system 100 for collecting testing data for different users for health conditions such as diabetes. The system 100 preferably includes one or more health-monitoring devices, which are in wireless communication with a mobile device 130. For example, the health-monitoring device allows testing of various characteristics of the user, such as devices that measure heart rate, blood pressure, glucose levels, weight, temperature, breathing rates, etc. The health-monitoring device is paired with a mobile device 130 via a wireless link. Once the pairing is established, the testing data from the health-monitoring device are passed to the mobile device 130, which runs software that performs detailed analysis, allows management of the data (e.g., storage), and provides other relevant information in a format that may be readily understood by a user of the mobile device 130. The software thus performs data management relating to test results for the user of the mobile device 130.

The mobile device 130 performs data analysis on data obtained from the health-monitoring device, as will be explained below. The mobile device 130 allows communication with a wide area network such as the Internet 140. The system 100 includes a server 150 that is coupled to a database 160. The server 150 maintains patient data in the database 160. Other users, such as health care providers, may have access to patient data in the database 160 via a network-connected device such as a personal computer 170.

There are multiple users who may access the server 150 via mobile devices such as the mobile device 130.

For example, the server 150 may be part of a centralized health care system that provides further processing or storage of data collected by the mobile device 130. The centralized health care system may provide a web-based or a client-server based front end to data-management software running on the mobile device 130. Additionally or alternatively, the data may be shared with health care providers (HCPs). Accordingly, to transfer data from the mobile device 130 to the server 150, the mobile device 130 may connect directly via an interface, for example, to a wireless network or a Wi-Fi hotspot to the network 140. Data encryption and authentication procedures may be employed to ensure data security. The mobile device 130 detects the presence of a wireless network or a Wi-Fi hotspot and automatically transfers data to the server 150 through a background process. Alternatively, the mobile device 130 may alert the user that access to the server 150 is available, and the user can initiate data transfer if desired.

The server 150 may be used for a variety of heath care functions. For example, the data may be shared with a health care professional for more effective visits. The data may be used for health monitoring of a user or remote patient care. The data may be used for life style programs. As will be explained below, the mobile device 130 may include other applications such as activity or fitness monitor applications that may interface with the application's data. The data may be used for motivational support tools from persons with diabetes. Other health care providers may receive selected data via other devices such as a server 180, a laptop 182, a personal computer 184, a tablet 186, or any other computing device that allows access to data from the database 160 for other health care services such as monitoring, marketing and provision of services and products.

Figure 2:
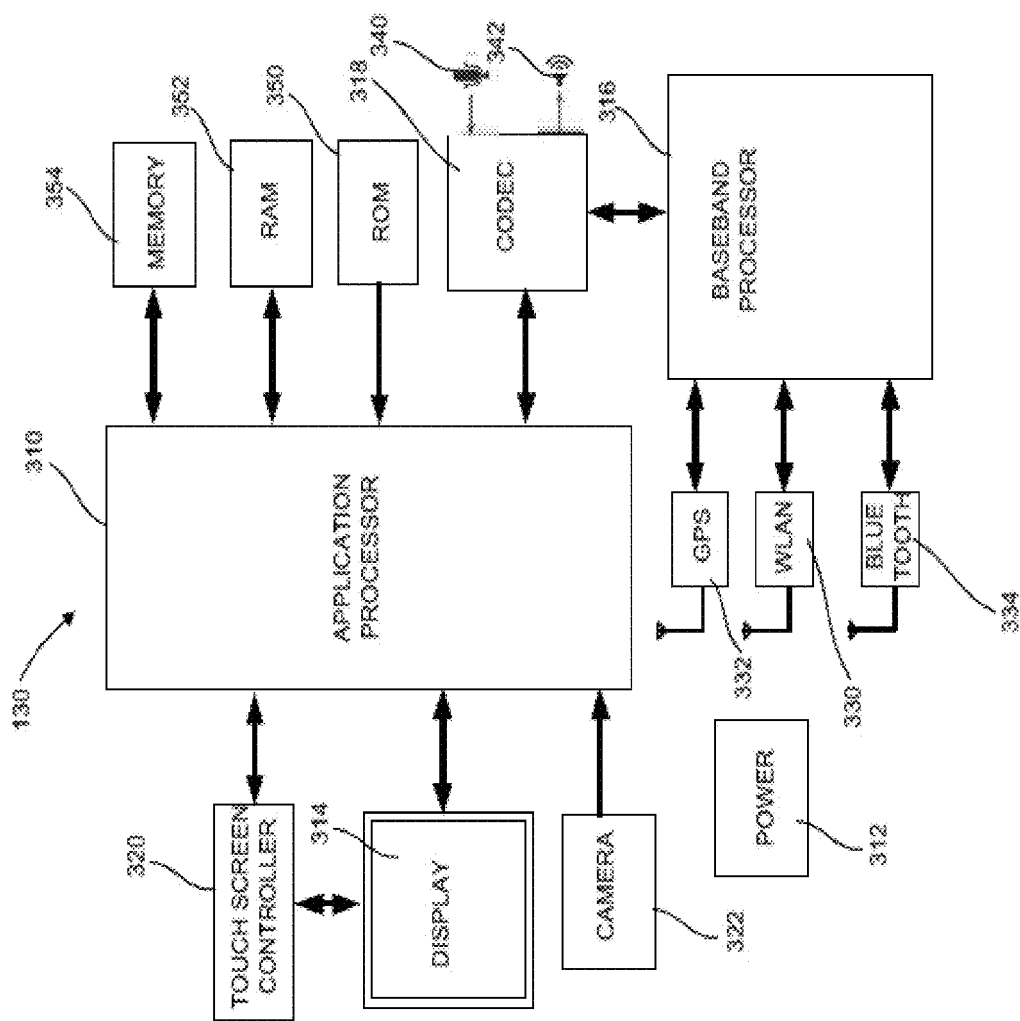
FIG. 2 illustrates a block diagram of a mobile device that displays relevant information relating to the results of analyte testing data transmitted wirelessly from the meter in FIG. 1.

FIG. 2 shows a block diagram of the mobile device 130 in FIG. 1 and runs the application described below for developing emergency communications in response to an urgent situation associated with the operator. In this example, the mobile device 130 may be virtually any preferably mobile computing device that is configured to send and receive information over a wireless communication medium, such as Bluetooth, with local devices. The mobile device 130 may be web-enabled and may run browser software for the presentation of web pages to the user. Such mobile user devices may include portable devices such as cellular telephones, smart-phones, display pagers, radio frequency (RF) devices, infrared (IR) devices, global positioning devices (GPS), Personal Digital Assistants (PDAs), handheld computers, wearable computers, tablet computers, integrated devices combining one or more of the preceding devices, and the like. The mobile device 130 may include multiprocessor systems, microprocessor-based, or programmable consumer electronics, and the like. As such, user devices running the application described below may range widely in terms of capabilities and features.

As exampled below, the web-enabled user devices may include a browser application enabled to receive and to send wireless application protocol messages (WAP), and/or wired application messages, and the like. In one example, the browser application is enabled to employ HyperText Markup Language (HTML), Dynamic HTML, Handheld Device Markup Language (HDML), Wireless Markup Language (WML), WMLScript, JavaScript, EXtensible HTML (xHTML), Compact HTML (CHTML), and the like, to display and/or send digital information.

The user devices may also include at least one client application that is configured to receive control data and/or content from another computing device via a network transmission. The client application may include a capability to provide and receive textual content, graphical content, video content, audio content, and the like. Moreover, the user devices may be further configured to communicate and/or receive a message, such as through a Short Message Service (SMS), direct messaging (e.g., Twitter), e-mail, Multimedia Message Service (MMS), instant messaging (IM), internet relay chat (IRC), mIRC, Jabber, Enhanced Messaging Service (EMS), text messaging, Smart Messaging, Over the Air (OTA) messaging, or the like, between or with another computing device, and the like.

The network 140 in FIG. 1 is configured to allow communications between one computing device and another computing device. The network 140 may be enabled to employ any form of computer readable media for communicating information from one electronic device to another. On an interconnected set of LANs, including those based on differing architectures and protocols, a router and/or gateway device acts as a link between LANs, enabling messages to be sent between computing devices. Also, communication links within LANs typically include twisted wire pair or coaxial cable, while communication links between networks may utilize analog telephone lines; full or fractional dedicated digital lines including T1, T2, T3, and T4; Integrated Services Digital Networks (ISDNs); Digital Subscriber Lines (DSLs); wireless links including satellite links; or other communication links known to those of ordinary skill in the art. Furthermore, remote computers and other related electronic devices can be remotely connected to either LANs or WANs via a modem and temporary telephone link.

The network 140 may further include any of a variety of wireless sub-networks that may further overlay stand-alone ad-hoc networks, and the like, to provide an infrastructure-oriented connection. Such sub-networks may include mesh networks, Wireless LAN (WLAN) networks, cellular networks, and the like. The network 140 may also include an autonomous system of terminals, gateways, routers, and the like connected by wireless radio links or wireless transceivers. These connectors may be configured to move freely and randomly and organize themselves arbitrarily, such that the topology of the network 140 may change rapidly and arbitrarily.

The network 140 may further employ a plurality of access technologies including 2nd (2G), 2.5, 3rd (3G), 4th (4G) generation radio access for cellular systems; WLAN; Wireless Router (WR) mesh; and the like. Access technologies such as 2G, 3G, 4G, and future access networks may enable wide area coverage for mobile devices, with various degrees of mobility. For example, the network 140 may enable a radio connection through a radio network access such as Global System for Mobile communication (GSM), General Packet Radio Services (GPRS), Enhanced Data GSM Environment (EDGE), Wideband Code Division Multiple Access (WCDMA), CDMA1100, and the like. The network 140 may also be constructed for use with various other wired and wireless communication protocols, including TCP/IP, UDP, SIP, SMS, RTP, WAP, CDMA, TDMA, EDGE, UMTS, GPRS, GSM, UWB, WiMax, IEEE 802.11x, and the like. In essence, the network 140 may include virtually any wired and/or wireless communication mechanisms by which information may travel between one computing device and another computing device, network, and the like.

FIG. 2 also illustrates a block diagram of the components of a mobile device such as the mobile device 130 in FIG. 1.

The mobile device 130 includes an application processor 310, a power source 312, a display 314, a baseband processor 316, and a CODEC 318. In this example, the display 314 is an LCD touch screen that allows the user to control the applications run by the application processor 310 via touch inputs as well as view graphics generated by the application processor 310. The display 314 is controlled by a touch screen controller 320. The application processor 310 may be coupled to various devices such as a camera 322 and other interfaces such as a communication port, etc.

The baseband processor 316 receives signals from a network transmitter receiver 330 allowing communications with the network 140 in FIG. 1, a geo-referencing receiver 332 that allows the reception of positioning data to determine the location of the mobile device 130, and a Bluetooth receiver 334 that allows communication with other Bluetooth-enabled devices. The baseband processor 316 processes in the signals and is coupled to the CODEC 318, which converts the signals for use by the application processor 310. The CODEC 318 also decodes audio signals received by a microphone 340 and encodes data signals for output by a speaker 342 for functions such as a telephone application run by the applications processor 310. It is contemplated that other audio devices such as a headset may be coupled through the CODEC 318.

The processors 310, 316 may be conveniently implemented using one or more general purpose computer systems, microprocessors, digital signal processors, microcontrollers, application specific integrated circuits (ASIC), programmable logic devices (PLD), field programmable logic devices (FPLD), field programmable gate arrays (FPGA), and the like, programmed according to the teachings as described and illustrated herein, as will be appreciated by those skilled in the computer, software, and networking arts.

The operating system software and other applications are stored on read only memory (ROM) 350, random access memory (RAM) 352 and a memory storage device 354 for access by the applications processor 310. In this example, the memory storage device 354 is flash memory, but other memory devices may be used. The applications stored on the memory storage device 354 include the emotional score data collection and broadcast application, which creates interface graphics on the display and interfaces with a browsing application. It is contemplated that other forms of applications may incorporate the principles explained below. In this example, the analysis application may be preloaded on the mobile device 130, or may be offered as an application that may be downloaded to the mobile device 130 from a network-connected device such as the server 150 via the network 140.

The memory storage device 354 includes a machine-readable medium on which is stored one or more sets of instructions (e.g., software) embodying any one or more of the methodologies or functions described herein. The instructions may also reside, completely or at least partially, within the memory storage device 354, the ROM 350, the RAM 352, and/or within the processors 310 or 316 during execution thereof by the mobile device 130. The instructions may further be transmitted or received over a network, such as the network 140 in FIG. 1 via the network transmitter receiver 330. While the machine-readable medium is shown in this example to be a single medium, the term "machine-readable medium" should be taken to include a single medium or multiple media (e.g., a centralized or distributed database, and/or associated caches and servers) that store the one or more sets of instructions. The term "machine-readable medium" can also be taken to include any medium that is capable of storing, encoding, or carrying a set of instructions for execution by the machine and that cause the machine to perform any one or more of the methodologies of the various embodiments, or that is capable of storing, encoding, or carrying data structures utilized by or associated with such a set of instructions. The term "machine-readable medium" can accordingly be taken to include, but not be limited to, solid-state memories, optical media, and magnetic media.

A variety of different types of memory storage devices, such as a random access memory (RAM) or a read only memory (ROM) in the system or a floppy disk, hard disk, CD ROM, DVD ROM, flash, or other computer readable medium that is read from and/or written to by a magnetic, optical, or other reading and/or writing system that is coupled to the processor, may be used for the memory or memories in the user device 130.

The data-management software running on the mobile device 130 may be a collection of programs or computer code that receives and processes measured data and/or other input from other devices, such as FITBIT™.

Data security may be used by employing the data storage (e.g., an embedded database) that can only be accessed or decrypted by the data-management software. Furthermore, the software may also include programs or components, such as user-authentication routines, that protect data integrity and security. When the data-management software launches, it may immediately prompt the user for a user ID and password, personal identification number (PIN), and/or other authentication information. The user is only allowed access to data on the mobile device 130 if the response to the security prompt corresponds with authentication information stored with the data-management system 100. A user-authentication routine may also be employed to permit data to be transferred from the mobile device 130 to the server 150.

Figure 3:
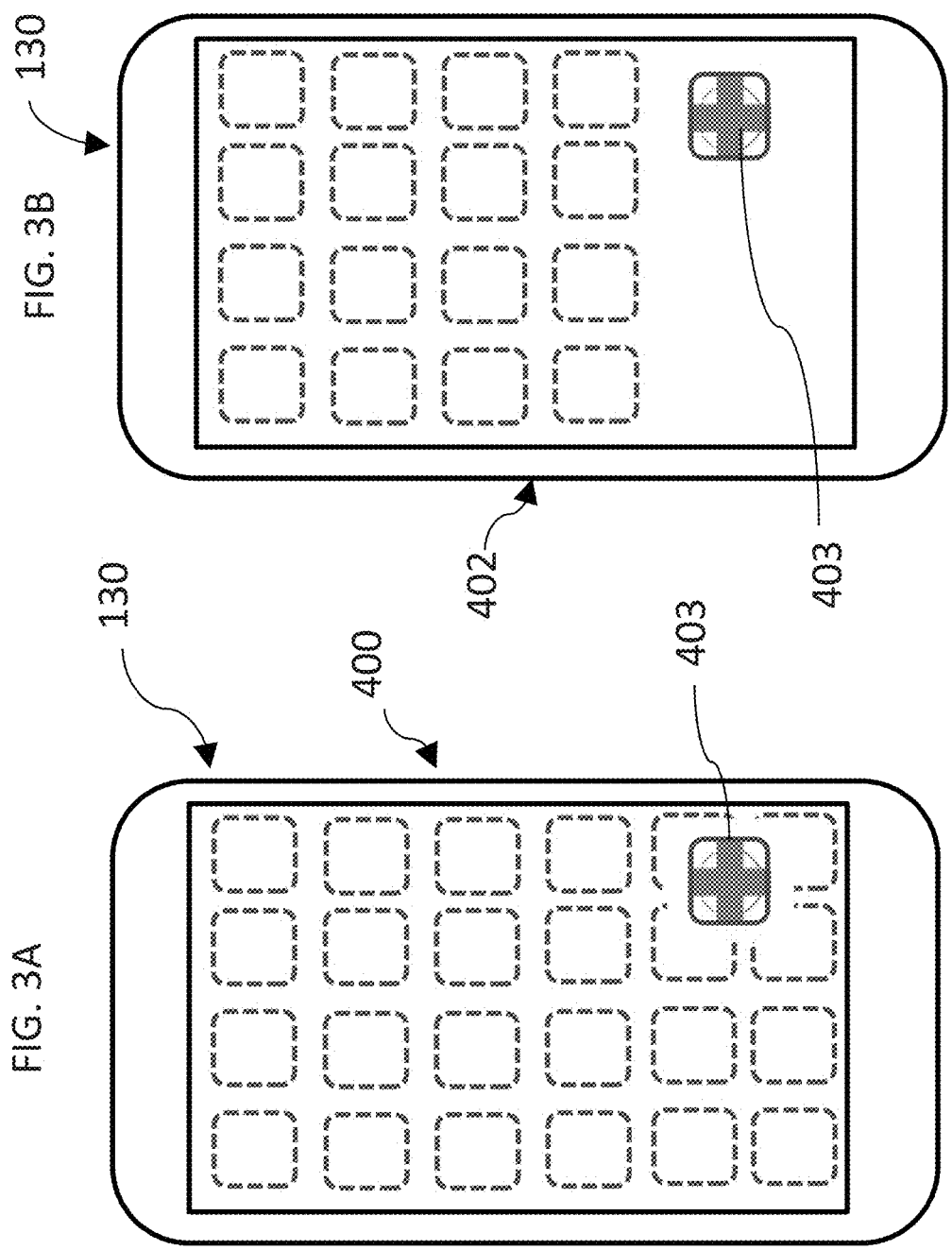
FIG. 3A illustrates a first display screen or page on a mobile device, locked or unlocked, and the emergency icon that initiates the application.
FIG. 3B illustrates a second display screen or page on a mobile device, locked or unlocked, and the emergency icon that initiates the application.

Additionally or alternatively, the transceivers 258 and 334 in FIGS. 2B and 3 respectively also may enable the health-monitoring device and the mobile device 130 to communicate via a radio-frequency (RF) link (e.g., a short-range RF telemetry), such as Bluetooth® wireless technologies, Zigbee, Z-Sense™ technology, FitSense, BodyLAN™ system, and other RF technologies. RF technologies such as Bluetooth® enable external devices to communicate wirelessly with, for example, laptop personal computers and mobile phones. Other wireless, or non-physical, communication technologies, such as infrared (IR) links, also may be used.

As described previously, the mobile device 130 may include a variety of interfaces to connect and communicate with a variety of devices. The mobile device 130 may employ its communication capabilities to connect remotely, e.g., over a network, with external systems to provide the user with a wider range of functionalities and features. In some embodiments, these external systems may provide a host function that manages the communication between the mobile device 130 and these external systems. These external systems may execute aspects of the data-management software or other software components stored on the mobile device 130 to enable the communication between the mobile device 130 and the external systems. Alternatively, these external systems may store the necessary software components locally.

Accordingly, the mobile device 130 may access the Internet or a cellular network, to transmit data remotely to other individuals. As such, a user does not have to connect the mobile device 130 directly with the other individual's processing devices to share data. The data stored on a mobile device 130 is therefore easily shared with other individuals, including emergency care specialists who may be located in distant or remote locations.

In addition, the mobile device 130 may connect to the network 140 to receive field upgrades to the data and/or software stored on the server 150. For example, the mobile device 130 may conveniently receive an updated/patched version, or even a completely new version, of the data-management software by connecting to a remote download server. As a further example, the mobile device 130 may receive new or updated parameters for the execution of software or applications on the mobile device 130. In some embodiments, new programs or features for the system 100 may be received, e.g., purchased, from a remote download server. Optional features that may customize or personalize the graphical user interface for the data-management application may be available through a system accessible through the Internet. To maintain the integrity of the data and software on the mobile device 130, data or software downloaded via field upgrade may be validated before being employed in the mobile device 130. For example, checksum routines may be employed to confirm that data or software has been successfully downloaded in its entirety. The mobile device 130 may include a processor that can locally execute software components to manage aspects of the field upgrade. For example, the processor on mobile device 130 may preserve data integrity on the mobile device 130 according to a data update file (DUF) or other component that ensures that the software has been successfully downloaded. For additional data security, the DUF be employed with data encryption/decryption.

The mobile device 130 may employ a USB interface to connect to a variety of devices. In conventional systems, standard USB is designed to provide connectivity between a processing device and peripheral devices, where the processing device acts as a host and the USB-enabled peripheral devices act as slaves. In general, with standard USB, only the USB host can initiate data transfers to the connected USB peripheral device, and the USB peripheral device can only respond to instructions given by the host. Thus, a USB-enabled peripheral device is not able to connect with other USB-enabled peripheral devices over a peer-to-peer communication channel.

FIGS. 3A and 3B illustrate, respectively, a basic home display screen 400 generated on the mobile device 130 and a secondary display screen 402. Through normal operation of the mobile device 130, the user moves between the various display screens 400, 402, each of which includes a plurality of icons associated with a particular app or function. As shown, the emergency icon 403 is constantly shown in the various display screens 400, 402, such that it is always present and capable of triggering the emergency application. The icon 403 can be moved by the user around the display screen to any point, as depicted with the two varying locations. The icon can be moved to any location so that it does not interrupt with varying tasks for which the device 130 is used. Once moved, the object will remain stationary at that point regardless of what state the phone is in, locked or unlocked. A locked state of the mobile device 130 is common in most mobile devices because it prohibits others from using a mobile phone. Although the mobile device 130 is shown as having only the basic home display screen 400 and the secondary display screen 402, it typically has many display screens and the number of display screens is customized by the user.

The emergency icon 403 is displayed on the screens at all times. It can be moved around the screen and placed anywhere on the screen by making a dragging motion via a touch screen input of the mobile device 130. Pressing on the emergency icon 403 for approximately one second or two seconds triggers the application. An option is available within the settings of the mobile device 130 that can change the size of the icon relative to the screen.

Figure 4:
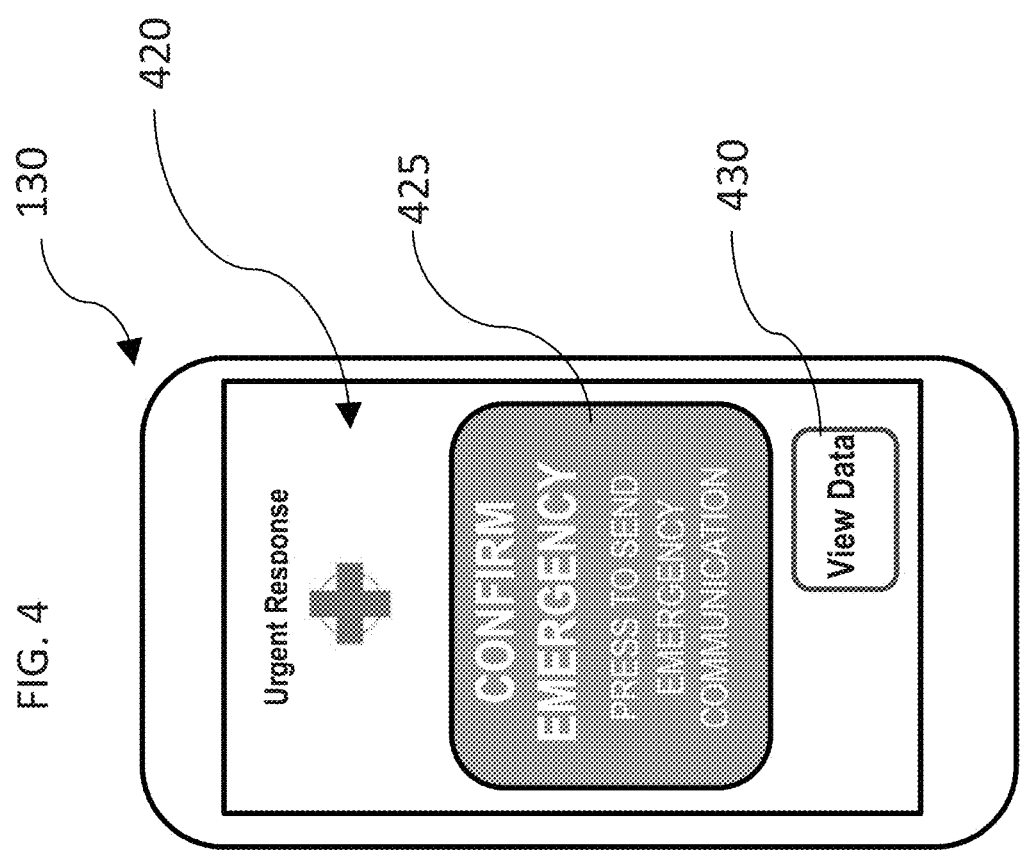
FIG. 4 illustrates an introductory screen for the emergency application that gives the user options to confirm the emergency or to view heath data options.

FIG. 4 illustrates an emergency screen display 420 generated on the mobile device 130 in response to the emergency icon 403 being triggered. A larger confirm-emergency button 425 is located within the emergency screen display 420 and, if pressed, the phone/text capabilities of the mobile device 130 are used to communicate with one or more third parties including an emergency number. The phone numbers for the third parties could include family contacts, close contacts, and/or neighbors that could provide assistance in the time of need. The contacts may further include a local ambulance service or another health care provider. The user customizes the list of contact numbers to be contacted when the emergency icon 403 (FIGS. 3A and 3B) is triggered. In one preferred embodiment, each of these numbers will receive a default emergency text once the confirm-emergency button 425 is triggered and, preferably, a shared GPS location if the application is able to use the location services of the mobile device 130.

FIG. 4 also illustrates a View Data button 430 that, when pressed, presents a data screen on the mobile device 130 to the user. In addition to the emergency icon 403 being available to the user at all times on the display screen, the application constantly receives input data from features already available on the mobile device 130 as well as other optional devices that can be linked via Bluetooth or Wi-Fi, such as heart-rate monitoring devices and blood-pressure monitoring devices. To the extend the user has aspects of his or her blood checked and recorded locally in the mobile device, that recorded data will be constantly monitored and stored by the application in case an emergency communication is requested via the emergency button 403 and the Confirming Emergency button 425. The View Data button 430 permits the user to view, on the display, the various health-related statistics and recommendations based of the monitoring devices (e.g., heart rate, blood pressure, etc.) that are connected to the mobile device 130 and, hence, the application. Because these other vital statistics are accessible by the application, each of the recipient texts receives the user's health-related statistics via a text as well, as shown in FIG. 6. Thus, the emergency screen display 420 may cause a series of texts (e.g., emergency notification, user location, user health statistics) providing information about the user to a plurality of designated contacts.

Figure 5:
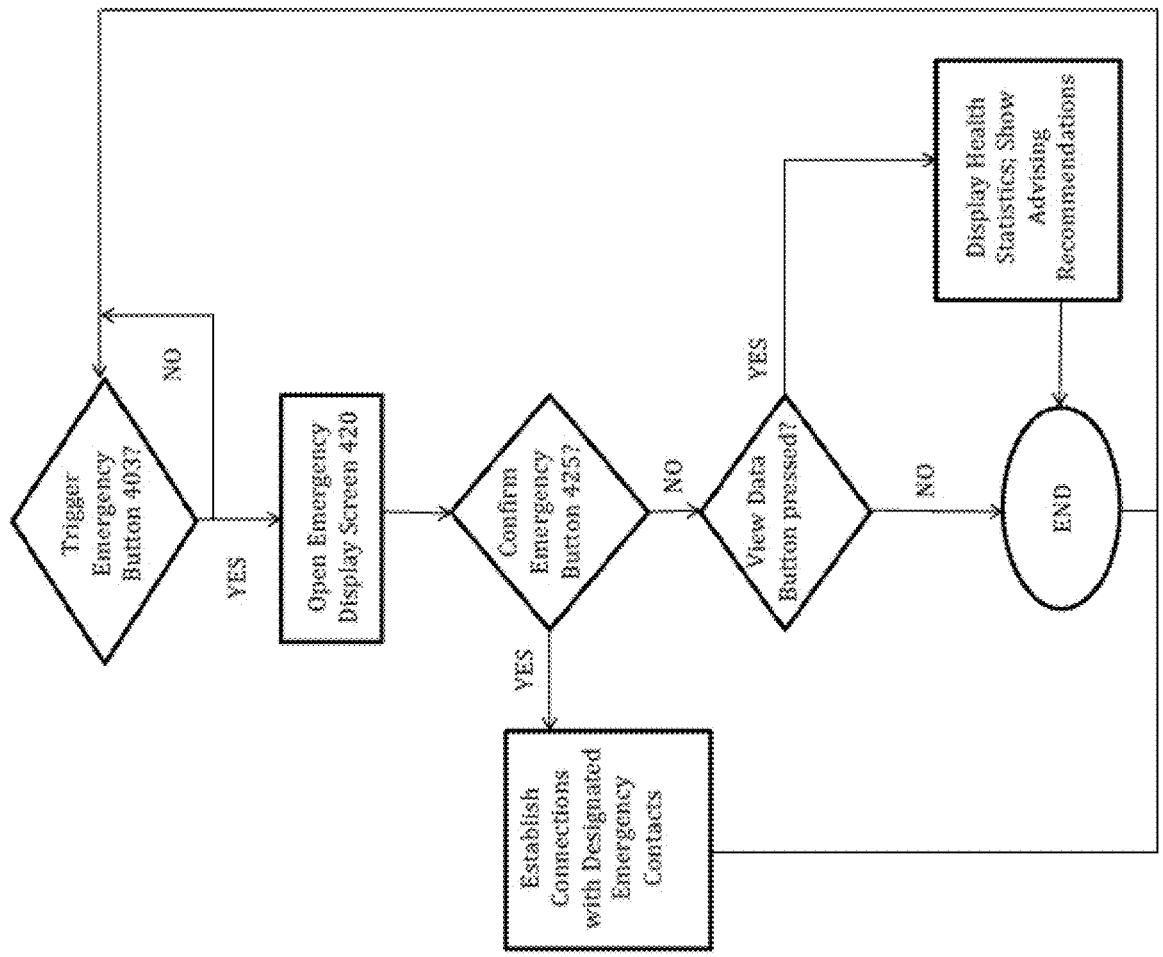
FIG. 5 illustrates a flow diagram of the operations of the application.

FIG. 5 illustrates a flow diagram of one exemplary process according to the present invention. The application continuously monitors the emergency button 403 to determine user is triggered emergency condition. If user has triggered the emergency button 403, then the emergency display screen (FIG. 4) is on the mobile device 130. At this point, the process continues in one of two ways. First, if the user actuates the Emergency Confirmation button 425, then the application establishes the connections with the various emergency contacts that the user has previously designated (See FIGS. 6A and 6B below). Second, the View Data page is displayed after the user actuates View Data button. After the initial display screen is shown, the display will remain in a constant state unless either the Emergency button or the View Data button is activated. After the View Data page is reviewed, the mobile device 130 returns to its normal display pages.

In an alternative embodiment, if the emergency button 403 is depressed and the mobile device 130 then remains motionless, then, after a short period time (e.g., 10 seconds) the mobile device 130 will actually and audio alarm to inform the user that the emergency button 403 has been pressed so that the user can cancel the emergency notification if the actuation of the emergency button 43 was inadvertent. If no activity is detected by the mobile device 130, then the user is assumed to be in a state of peril and the emergency application proceeds to automatically establish connection with the emergency contacts.

In another aspect of the present invention, if the mobile device 130 contains an accelerometer, the application is also linked to the output of the internal accelerometer to sense various movements. One particular output from the accelerometer that is checked is an output associated with a human fall. The application contains parameters that can differentiate between a typical dropping of a mobile device 130 as opposed to the fall of a human who has mobile device 130 in his or her possession (in a pocket or in a hand). If the application detects that a human fall, an alert message is displayed and preferably an audio message/alarm is produced by the mobile device to alert the user that a human-fall output has been detected. The alert message preferably contains a countdown for the user so as to provide an opportunity for deactivation (e.g., "A fall has been detected. Emergency contacts will be contacted in 10 seconds, 9 seconds, 8 seconds, . . . " etc.). If the application does not receive a response from the individual before the countdown expires, then the application automatically contacts the third parties with an emergency message via the mobile device's mobile network in the same manner as described above with reference to FIGS. 1-5 when the large Confirm-Emergency 425 is activated. Once a phone connection is initiated with the third party, the speakerphone capability of the device will be automatically triggered for receiving voice inputs from user so as to permit communication with the third party, who will use his or her judgment to determine further action. Alternatively, if the user is unable to provide any verbal response, the emergency application then proceeds to indicate a pre-recorded audio message from the user as discussed below relative to FIG. 6.

The output of the accelerometer can also be used in an automobile-crash scenario to activate the application. As the application contains location-detection parameters, when the GPS indicates movement commonly associated with an automobile, a certain deceleration or shock at that time is likely associated with an automobile crash. If the application detects such a crash, an alert message is displayed on the mobile device 130 and preferably an audio message/alarm is produced by the mobile device to alert the user that a crash has been detected. The alert message contains a countdown for the user so as to provide an opportunity for deactivation (e.g., "A crash has been detected. Emergency contacts will be contacted in 10 seconds, 9 seconds, 8 seconds, . . . " etc.). If the user is unable to provide any verbal response and manual input to the mobile device 130, the emergency application then proceeds to indicate a pre-recorded audio message from the user as discussed below relative to FIG. 6.

As mentioned above, if the application is able to connect to a heart-rate sensor through the mobile device 130 or through another device that is connected through Bluetooth or Wi-Fi, the individual's heart rate and/or blood pressure will be monitored and the corresponding data will be stored by or testable by the application. The application may also contain parameters of a healthy heart rate. If the individual's heart rate exceeds the range of healthy heart rates, an alert message is displayed on the mobile device 130 in a manner similar to the condition of the user activating the emergency icon 403 in FIGS. 3A and 3B. The individual is then encouraged to seek medical advice and is given an option to be connected to a third-party emergency responder. Once a connection is established with the third party, the speakerphone of the mobile device 130 capability of the device will be triggered and the third party individual will use judgment to determine further action.

Figures 6A, 6B:
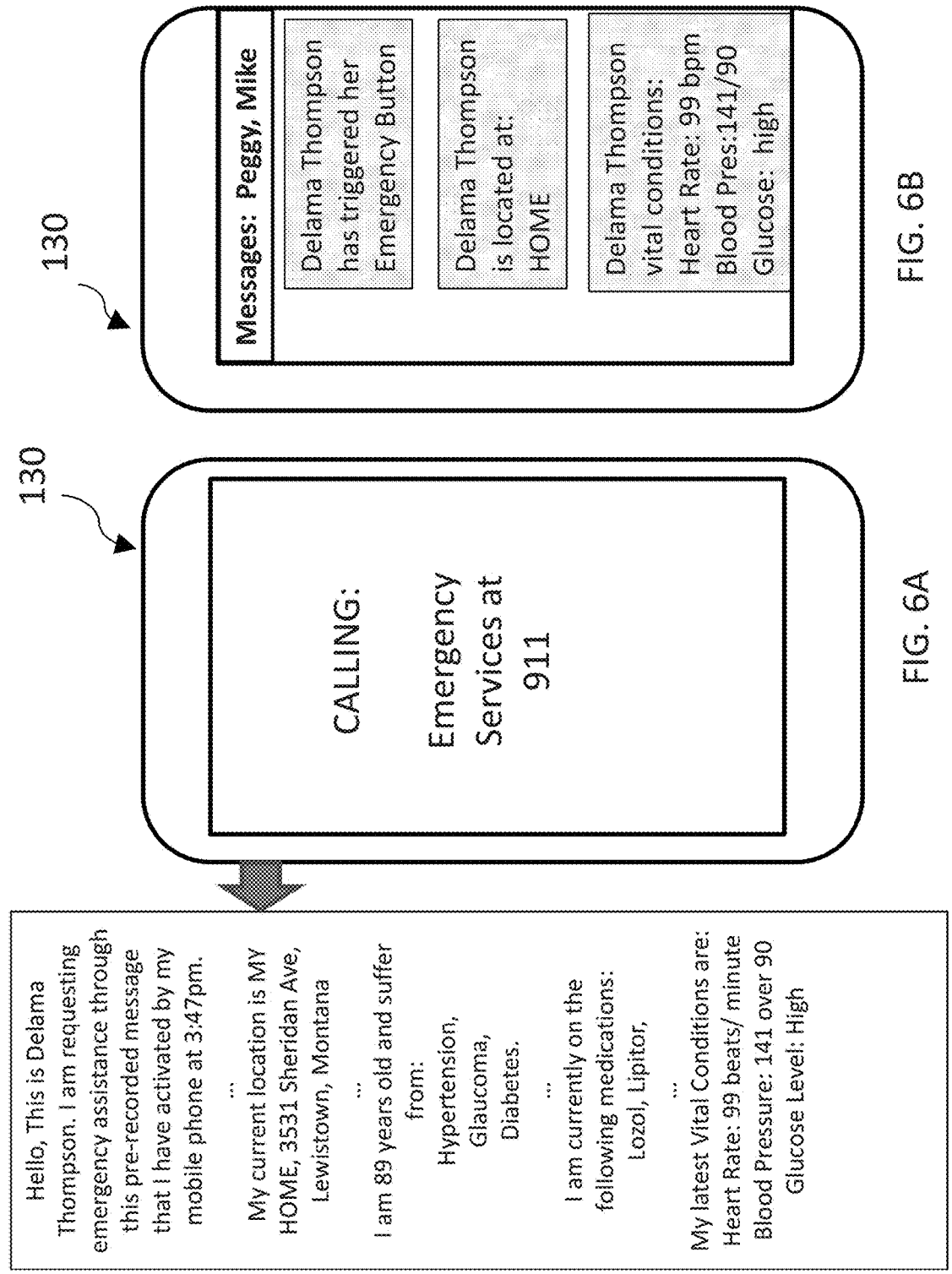
FIG. 6A schematically illustrates an emergency phone call to the designated emergency contact number that has been initiated by the user, which includes the transmission of a prerecorded audio message from the user.
FIG. 6B schematically illustrates emergency text messages that are sent by the user to one or more designated contacts to instruct them that the user has initiated the emergency application on his or her mobile device.

FIGS. 6A and 6B schematically illustrate the types of communication that may occur once the user has actuated the Confirm Emergency button 425 (FIG. 4) or, perhaps, if the mobile device 130 remains motionless and receives no input from the user after the user has depressed the Emergency button 403. The application proceeds to make at least one emergency phone call and, possibly, sent out text messages to one or more designated recipients. As shown in FIG. 6A, if the user is unable to provide a real-time verbal communication to the emergency number that has been called, then the application proceeds to communicate a prerecorded message from a user, as graphically illustrated on the left hand side of FIG. 6A. If the user has designated emergency service number (e.g., 911) as the public emergence service to dial for him or her, that when the operator at the emergency service provider picks up the call, he or she will hear the prerecorded message that provides the necessary information that is required for emergency services personnel to make a emergency visit to the user. In particular, the prerecorded message provides information about the name of the user, the age of the user, the location of the user, the user's known medical conditions, the user's current medications, the time the user triggered the emergency button, and/or the user's vital conditions as measured by various monitoring devices that are coupled to the mobile device 130. The message may repeat two or three times to ensure that the operator of the emergency service provider gains the appropriate information.

With regard to the location of the user, because the mobile device 130 can travel with the user to many different locations, the application continuously monitors the current location of the user in case the user actuates the emergency application and, therefore, wants to communicate his or her location. The location of the mobile device 130 can be accomplished in different ways. In one example, the application determines the location of the mobile device 130 through the GPS functionality associated with the mobile device 130. This location can be indicated in terms of known coordinates, such as longitude and latitude coordinates. The longitude and latitude coordinates can be further refined to known specific locations associated with those coordinates. Alternatively, because the mobile device 130 is often communicating through its Wi-Fi functionality, the user can use the settings feature of the application to indicate a street address location associated with the various known Wi-Fi connections. As an example, the user can store his or her home address in association with the user's home Wi-Fi network. Accordingly, when the mobile device 130 is communicating with the user's Wi-Fi network, then the emergency application determines that the user's current location is in his or her home, which has the street address that has been previously designated by the user in the application. Accordingly, in a prerecorded voice message of FIG. 6A, the current location is indicated to be the user's "HOME," but that portion of the recorded message can be substituted for other locations, such as mobile device's GPS coordinates, addresses or locations associated with the GPS coordinates, or addresses or locations associated with other Wi-Fi networks that have been stored by the user in the application. While the main portions of the prerecorded audio message can be recorded in the user's own voice, certain segments of the prerecorded message that are variable can be communicated in a standardized voice, such as the user's current location or the user's vital signs as measured by monitoring devices in communication with the mobile device 130.

FIG. 6B illustrates the text messages that are automatically sent to the user's designated contacts. In illustrated embodiment, the application is automatically sending text messages to two individuals ("Peggy" and "Mike") to inform them that she has triggered the Emergency buttons 403, 425 on her mobile device 130. The designated contacts are typically a neighbor, a spouse, a sibling, a child, and/or an emergency health-care provider who are aware of the user's current medical conditions and the potential problems that he or she faces. The first text message simply informs the designated recipients that the user has activated the emergency button. The second text message to designated recipients of the user's location, which is known from the GPS coordinates of the mobile device 130 or a Wi-Fi network in communication with the mobile device 130 when the emergency application is actuated. The third text message from the user informs the designated recipients of the user's vital statistics, as measured by the mobile device 130 or other monitor devices coupled to the mobile device 130. The present invention contemplates more or less numbers of texts communicate to the designated recipients. For example, the application may only communicate the fact that the emergency button has been triggered, or only net emergency button has been triggered and the user's location. Alternatively, after the initial text message indicating that the emergency button has been actuated, one or more text messages may include information about the fact that the mobile device 130 has detected that the user may have fallen, or that the user may have been involved in an automobile accident.

Figure 7B:
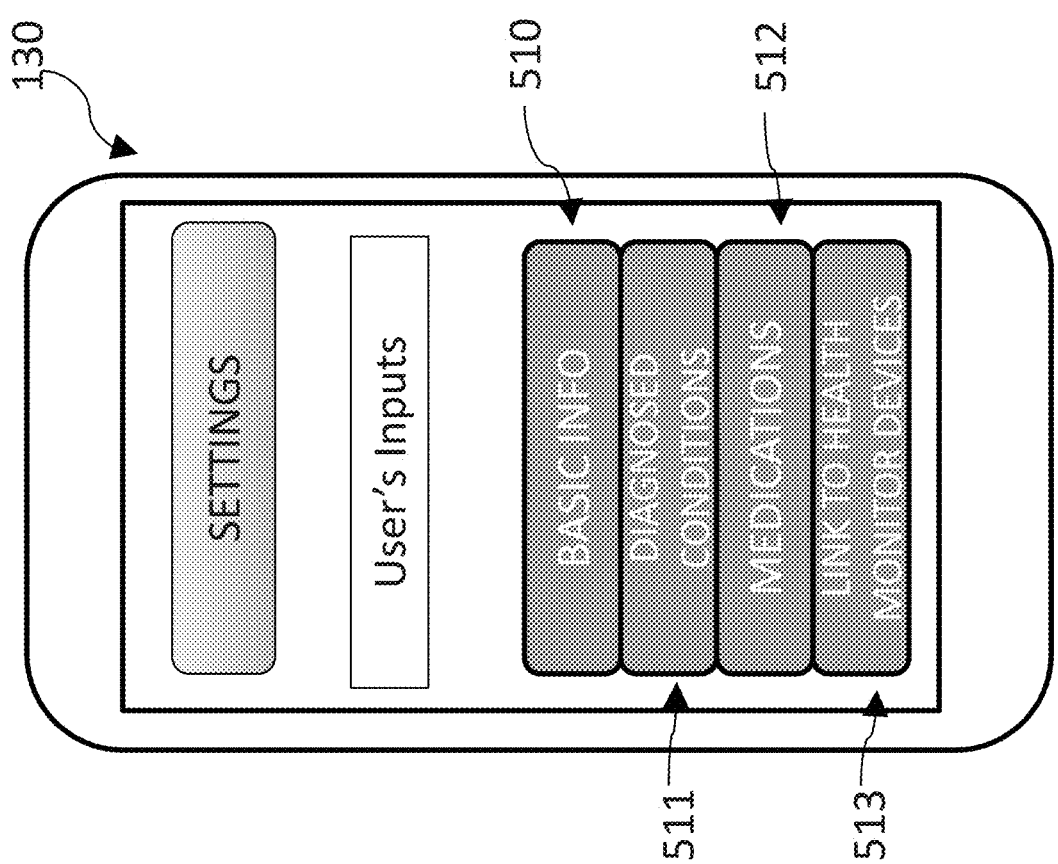
FIG. 7B illustrates a second settings screen associated with the emergency application that permits the user to enter various pieces of information, such as health information about the user, medication taken by the user, Wi-Fi networks and associated street addresses commonly used by the user, and pre-recorded messages that can be communicated in automatic phone call.

FIGS. 7A and 7B illustrate examples of a settings screen that is displayed on the mobile device 130 during a setup mode for the application. As shown in FIG. 7A, the settings screen provides the user with the ability to add, modify, and/or delete designated recipients of the text messaging and/or the emergency call service, examples of which are illustrated in FIGS. 6A and 6B. The settings screen allows the user to manipulate the emergency contacts list used by the application during an emergency. FIG. 7A illustrates four of the functions that this screen can perform, although other set-up functions can be used. The View button 500 allows the user to simply view the current customized list of emergency alert recipients. The Add button 201 allows the user to input a new emergency name and number, while the Delete button 203 allows the user to delete an emergency contact. Finally, the Edit button 502 allows the user to view and make changes to any existing contact.

FIG. 7B allows the user to input his or her personal information that can be used for communication during an emergency event. The Basic Information button 510 allows the user to input his or her basic information, such as age, weight, gender, address location, etc. The Diagnosed Conditions button 511 permits the user to input his or her currently known medical conditions, such as hypertension, glaucoma, shingles, Alzheimer's, etc. The Medications button 512 permits the user to input a list of medications (both over-the-counter and prescription) that he or she currently takes for medical conditions. The Link to Health Monitor Devices button 513 permits the user to enter various monitoring devices that he or she has linked to the mobile device 130 for monitoring and recording various health conditions, such as heart rate, blood pressure, etc. FIGS. 7A and 7B provide only examples of information that can be entered; other information (e.g., address location of particular Wi-Fi connections that are commonly used by the user) that is described above relative to the present invention can be entered through the application's setup mode. Accordingly, the user is able to tailor the application to his or her specific conditions and intended use. All of the information provided in the setup mode provides critical information that can be immediately communicated to the designated contacts and emergency health-care responders by the user in response to the user triggering the emergency button of the application.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention.

I claim:
1. A computer-implemented method for communicating an emergency condition of a user by use of a mobile device, the mobile device having network communication functionalities, the method comprising:
by use of an emergency mobile app stored on the mobile device of the user, displaying a first on-screen button for the user to actuate in response to an emergency condition, the first on-screen button being displayed on each of a plurality of display pages of the mobile device, each of the plurality of display pages including multiple on-screen buttons associated with apps or functions, the first on-screen button floating over other ones of the multiple on-screen buttons on the plurality of display pages such that the first on-screen button is visually displayed over the other ones of the multiple on-screen buttons;
in response to actuation of the first on-screen button by the user, displaying a confirm-emergency button associated with the emergency mobile app to ensure that the user intends to send emergency communications; and
in response to actuation of the confirm-emergency button by the user, automatically communicating, by use of the mobile device, (i) a plurality of text messages to a plurality of designated recipients indicating that the user has encountered the emergency condition, and (ii) a phone call to a designated public-safety organization from which the user is requesting an emergency service,
wherein, in response to the mobile device receiving no voice input from the user after the actuation of the emergency button, the phone call including a pre-recorded audio message that is recorded prior to actuation of the emergency button, the pre-recorded audio message includes a location portion that indicates the user's location when the user actuated the emergency button, the location portion of the pre-recorded audio message being selected from a plurality of possible location portions that have been pre-recorded prior to actuation of the emergency button.

2. The method of claim 1, wherein the phone call is a live phone call that automatically actuates a speakerphone functionality of the mobile device.

3. The method of claim 1, wherein the plurality of designated recipients who receive the text message include at least two of the following (i) a neighbor, (ii) a spouse, (iii) a sibling, and (iv) a child.

4. The method of claim 1, further including, by use of the emergency mobile app stored on the mobile device of the user, storing mobile-device contact information for each of the plurality of designated recipients and for the designated public-safety organization.

5. The method of claim 4, further including, by use of the emergency mobile app stored on the mobile device of the user, displaying an emergency-contacts set-up page that permits the user to modify contact information related to the plurality of designated recipients and for the designated public-safety organization.

6. The method of claim 1, wherein, in response to the actuation of the confirm-emergency button by the user, automatically communicating, by the mobile device, a second plurality of text messages to the plurality of designated recipients indicating that location of the user as determined by a Wi-Fi detection signal or a GPS-location signal associated with the mobile device.

7. The method of claim 6, further including, by use of the emergency mobile app stored on the mobile device of the user, storing the street-address location associated with a particular Wi-Fi detection signal such that the Wi-Fi detection signal serves as a location identifier in the event that the user actuates the confirm-emergency button.

8. The method of claim 1, wherein the plurality of text messages are in the form of a single group text message to the plurality of designated recipients.

9. The method of claim 1, wherein the mobile device includes an accelerometer or communicates with monitoring device of the user that includes an accelerometer, and the method further includes, in response to acceleration data from the accelerometer indicating a potential fall or accident by the user, automatically communicating via the text message or that phone call that the potential fall or accident has occurred.

10. A computer-implemented method for communicating an emergency condition of a user by use of a mobile device, the mobile device having network communication functionalities, the method comprising:
by use of an emergency mobile app stored on the mobile device of the user, displaying an emergency button for the user to actuate in response to an emergency condition, the emergency button being displayed on each of a plurality of display pages of the mobile device;
receiving, from a monitor device, health-related data associated with the user, the monitor device including a wireless transceiver for communicating with the mobile device;
by use of the emergency mobile app stored on the mobile device of the user, accessing the health-related data of the user;
in response to actuation of the emergency button by the user, automatically communicating, by use of the mobile device, (i) a phone call to a designated public-safety organization from which the user is requesting an emergency service, and (ii) a plurality of text messages to a plurality of designated recipients indicating that the user has encountered the emergency condition, the plurality of text messages including texts that provides the current health-related data of the user,
wherein, if no voice input from the user is received by the mobile device after the actuation of the emergency button, the phone call includes a pre-recorded audio message that is recorded prior to actuation of the emergency button, the pre-recorded audio message includes a location portion that indicates the user's location when the user actuates the emergency button, the location portion of the pre-recorded audio message being selected from a plurality of possible location portions that have been pre-recorded prior to actuation of the emergency button.

11. The method of claim 10, wherein, in response to actuation of the emergency button by the user, automatically communicating, by the mobile device, a second plurality of text messages to the plurality of designated recipients indicating that location of the user as determined by a Wi-Fi detection signal or a GPS-location signal.

12. The method of claim 10, wherein the prerecorded audio message includes the health-related data of the user.

13. A computer-implemented method for communicating an emergency condition of a user by use of a mobile device, the method comprising:
downloading, to the mobile device, an emergency mobile app;
by use of an input device associated with the mobile device, receiving and storing user information for the emergency mobile app that can be used for emergency communications in the event of a future emergency condition, the user information including contact information for contacts that are to be contacted in the event of a future emergency condition, the user information including health-related information that corresponds to the user's health condition, the user information further including a plurality of pre-recorded audio messages that indicate a plurality of different user locations and that are recorded prior to an emergency situation;
displaying, on the display screen of the mobile device, an emergency button associated with the emergency mobile app, the emergency button being actuatable by the user in response to an emergency condition, the emergency button being displayed on each of a plurality of display pages of the mobile device;
after the emergency button has been actuated, automatically communicating, by the mobile device, (i) a plurality of text messages to at least one designated recipient indicating that the user has encountered the emergency condition, and (ii) a phone call to a designated public-safety organization from which the user is requesting an emergency service, at least one of the plurality of text messages and the phone call including the health-related information that was previously entered by the user via the emergency mobile app,
and wherein in response to the mobile device receiving no voice input from the user after the actuation of the emergency button, the phone call to the designated public-safety organization includes one of the plurality of pre-recorded audio messages that is associated with the user's location at the time of the actuation of the emergency button as determined by a Wi-Fi detection signal or a GPS-location signal received by the mobile device.

14. The method of claim 13, wherein, in response to actuation of the emergency button by the user, automatically displaying a confirm-emergency button associated with the emergency mobile app to ensure that the user intends to send emergency communications, the automatic communicating of the plurality of text messages and the phone call occurring in response to the actuation of the confirm-emergency button.

15. The method of claim 13, wherein the health-related information includes data from a health-monitoring device that is linked to the mobile device.

16. The method of claim 13, wherein the health-related information includes the user's current diagnosed medical conditions or medications.

17. The method of claim 13, wherein the plurality of text messages are in the form of a single group text message to a plurality of designated recipients.

18. The method of claim 13, wherein the prerecorded audio message includes the health-related information of the user.

* * * * *